(12) United States Patent
Vo et al.

(10) Patent No.: US 7,930,705 B2
(45) Date of Patent: Apr. 19, 2011

(54) ENVIRONMENT FOR EXECUTING LEGACY APPLICATIONS ON A NATIVE OPERATING SYSTEM

(75) Inventors: Hoi Huu Vo, Bellevue, WA (US); Samer N. Arafeh, Sammamish, WA (US)

(73) Assignee: Microsoft Corporation, Redmond, WA (US)

( * ) Notice: Subject to any disclaimer, the term of this patent is extended or adjusted under 35 U.S.C. 154(b) by 1047 days.

(21) Appl. No.: 11/697,398

(22) Filed: Apr. 6, 2007

(65) Prior Publication Data

US 2008/0034377 A1    Feb. 7, 2008

(51) Int. Cl.
  G06F 3/00    (2006.01)
  G06F 9/44    (2006.01)
  G06F 9/46    (2006.01)
(52) U.S. Cl. .................................. 719/328; 719/320
(58) Field of Classification Search ................. 719/320, 719/328
  See application file for complete search history.

(56) References Cited

U.S. PATENT DOCUMENTS

| | | | |
|---|---|---|---|
| 6,182,158 B1 | 1/2001 | Kougiouris et al. | 709/328 |
| 6,314,560 B1 | 11/2001 | Dunn et al. | 717/5 |
| 6,336,146 B1 | 1/2002 | Burridge et al. | 709/310 |
| 6,502,237 B1 | 12/2002 | Yates et al. | 717/136 |
| 6,675,229 B1 | 1/2004 | Bruno et al. | 709/328 |
| 7,124,398 B2 | 10/2006 | Chen et al. | 717/106 |
| 7,581,045 B2 * | 8/2009 | Wiegert et al. | 710/61 |
| 2001/0037417 A1 * | 11/2001 | Meyer | 709/332 |
| 2003/0188043 A1 * | 10/2003 | Woodall et al. | 709/328 |
| 2004/0181785 A1 | 9/2004 | Zwirner et al. | 717/140 |
| 2005/0050076 A1 | 3/2005 | Tong et al. | 707/100 |
| 2005/0097521 A1 | 5/2005 | Liu | 717/136 |
| 2005/0172263 A1 | 8/2005 | Hariharan et al. | 717/109 |

OTHER PUBLICATIONS

"MIcrosoft Computer Dictionary", Microsoft Press, Fifth Edition, p. 499.*
Cifuentes, C. et al., "Binary Translation: Static, Dynamic, Retargetable?", http://www.csee.uq.edu.au/~cristina/icsm96.ps, 8 pages, 1996.
Cifuentes, C. et al., "The Design of a Resourceable and Retargetable Binary Translator", http://www.cs.virginia.edu/"~nr/pubs/wcre99.ps, 12 pages, 1999.
Gal, A. et al., "Executing Legacy Applications on a Java Operating System", http://www.betriebssysteme.org/plos/papers/gal.pdf, 1 thru 5, 2004.

* cited by examiner

*Primary Examiner* — Qing Wu
(74) *Attorney, Agent, or Firm* — Woodcock Washburn LLP

(57) ABSTRACT

An application compatibility module is disclosed that provides compatibility between legacy binary system modules ("legacy binaries") and a native operating system. The application compatibility module therefore allows legacy applications to execute within the native operating system, while still using their corresponding legacy binaries. The application compatibility module may provide compatibility between legacy binaries and the native operating system by translating communications between the legacy binaries and the native operating system.

18 Claims, 7 Drawing Sheets

ENVIRONMENT FOR EXECUTING LEGACY APPLICATIONS ON A NATIVE OPERATING SYSTEM

BACKGROUND

An operating system is the foundational software of a computer that may perform a wide variety of operations such as scheduling tasks, allocating storage, and interacting with various applications. Because they are so vital to the computers on which they execute, operating systems are often updated to provide a number of new and improved features. An operating system may be updated by releasing a new version of the operating system. For example, the Windows operating system from MICROSOFT Corp. of Redmond, Wash. has been released in a number of versions such as Windows Vista, Windows XP, Windows Me and Windows 2000. A newest version of an operating system may be referred to as a "native" system, while previous versions of the operating system may be referred to as "legacy" systems. Native systems may offer may offer several advantages to consumers in comparison with their legacy counterparts.

One problem related to updating of operating systems is that legacy binary programming modules ("legacy binaries") designed to execute with legacy applications may not be completely compatible with the native operating system. In particular, a native operating system may be incapable of understanding and/or handling many of the legacy system calls that are made by legacy binaries. For example, in some cases, a legacy system call that once existed in a legacy operating system may no longer be valid in the native operating system. In other cases, a legacy system call may have a counterpart native system call, but the counterpart native system call may not be completely identical to the legacy system call. In addition to system calls, legacy binaries may be incapable of understanding and/or handling many of the callbacks and exceptions that are generated by a native operating system. For example, a native callback may implement behaviors that do not map to any existing legacy callback functions. Additionally, for example, the native operating system may generate an exception using a new layout that is not compatible with the legacy binaries.

One conventional approach to the legacy binary compatibility problem is to use native binaries rather than legacy binaries, and to load a "shim" program that sits between the legacy application and the native binaries. The shim program essentially translates various communications between the legacy application and the native binaries to provide compatibility between the legacy application and the native binaries. While shims offer a simple approach to alleviating the legacy binary compatibility problem, they also suffer from a number of limitations. In particular, shims are generated on an application-by-application basis and, therefore, lack scalability for large quantities of legacy applications.

Another conventional approach to the legacy binary compatibility problem is to execute the legacy application on a virtual machine that completely boots and runs on the legacy operating system. Enabling the legacy application to execute on a guest legacy operating system reduces the need for the legacy binaries to interact with the host native operating system. However, the use of virtual machines also creates several unwanted side effects by isolating the guest legacy operating system from the host native operating system, thereby making it difficult for the legacy application to access and share the resources of the host operating system.

Accordingly, what is needed is a scalable approach to the legacy binary compatibility problem that enables legacy binaries to interact efficiently with a native operating system while at the same time not restricting the accessibility of the native operating system's resources to the legacy application.

SUMMARY

An application compatibility module is disclosed that provides compatibility between legacy binary system modules ("legacy binaries") and a native operating system. The application compatibility module therefore allows legacy applications to execute within the native operating system, while still using their corresponding legacy binaries. The application compatibility module may provide compatibility between legacy binaries and the native operating system by translating communications between the legacy binaries and the native operating system. In particular, the application compatibility module may receive system calls from the legacy binaries and translate the system calls into formats that can be understood and processed by the native operating system. Additionally, the application compatibility module may receive callbacks and exceptions from the native operating system and translate the callbacks and exceptions into formats that can be understood and processed by the legacy binaries.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The illustrative embodiments will be better understood after reading the following detailed description with reference to the appended drawings, in which.

DETAILED DESCRIPTION

The inventive subject matter is described with specificity to meet statutory requirements. However, the description itself is not intended to limit the scope of this patent. Rather, it is contemplated that the claimed subject matter might also be embodied in other ways, to include different steps or combinations of steps similar to the ones described in this document, in conjunction with other present or future technologies.

Figure 1:
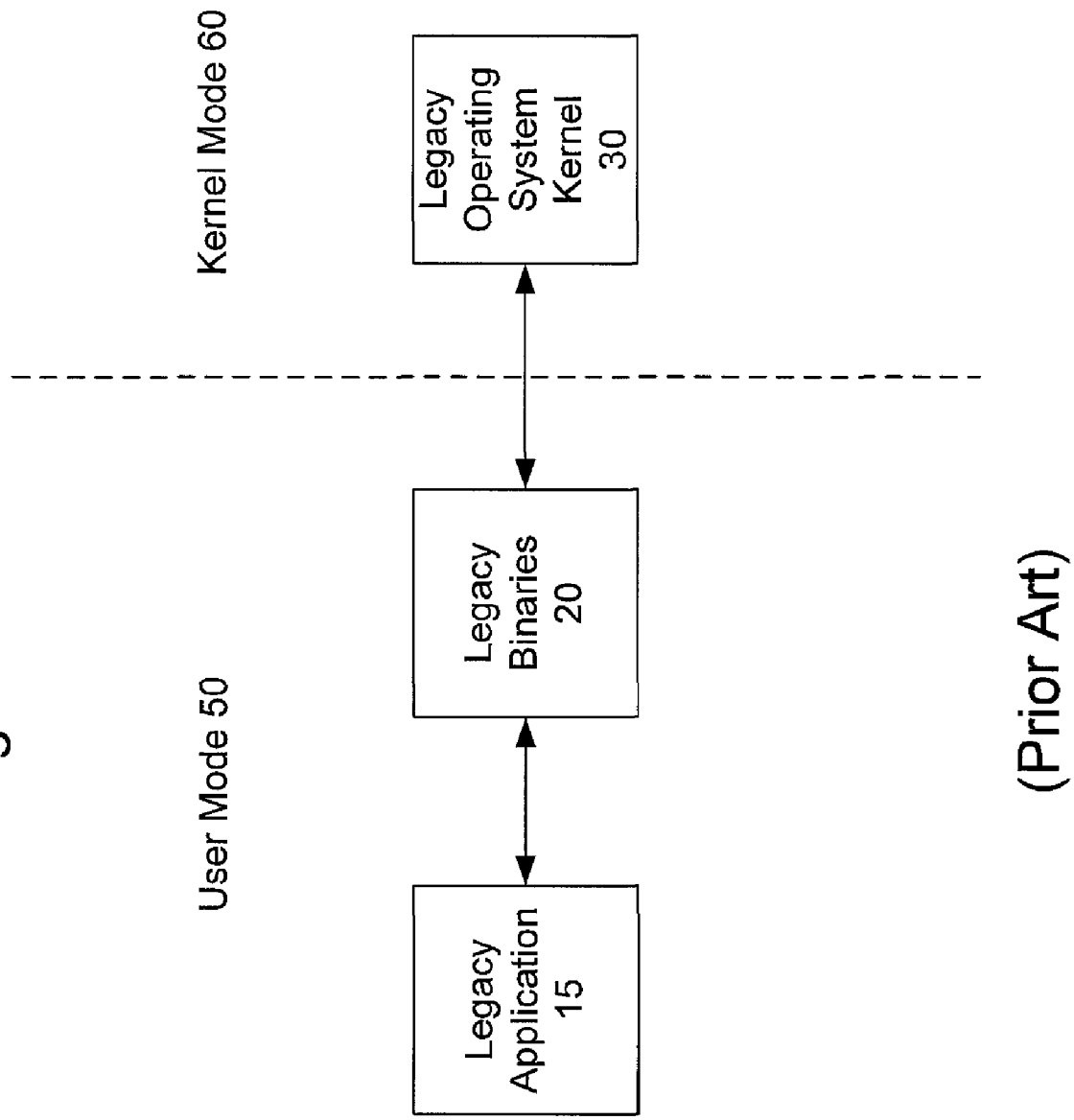
FIG. 1 depicts an exemplary execution stack for a legacy application executing within a legacy operating system.

Typically, an application will execute in combination with an operating system kernel and one or more binary program modules (hereinafter "binaries") that sit between the application and the operating system kernel to process communications between the application and the operating system kernel in some manner. When an application executes within an operating system for which it is designed, the application, the operating stem kernel, and the intermediate binaries will likely be compatible with one another. To illustrate this concept, an exemplary execution stack for a legacy application executing within a compatible legacy operating system is shown in FIG. 1. Legacy application 15 executes in user mode 50 along with legacy binaries 20, while legacy operating system kernel 30 executes in kernel mode 60. Legacy binaries 20 process communications between legacy application 15 and legacy operating system 30. Legacy binaries may include, for example, a network support function module and a process loader module that loads other binaries that are necessary or desirable for execution in combination with the legacy application 15.

Figure 2:
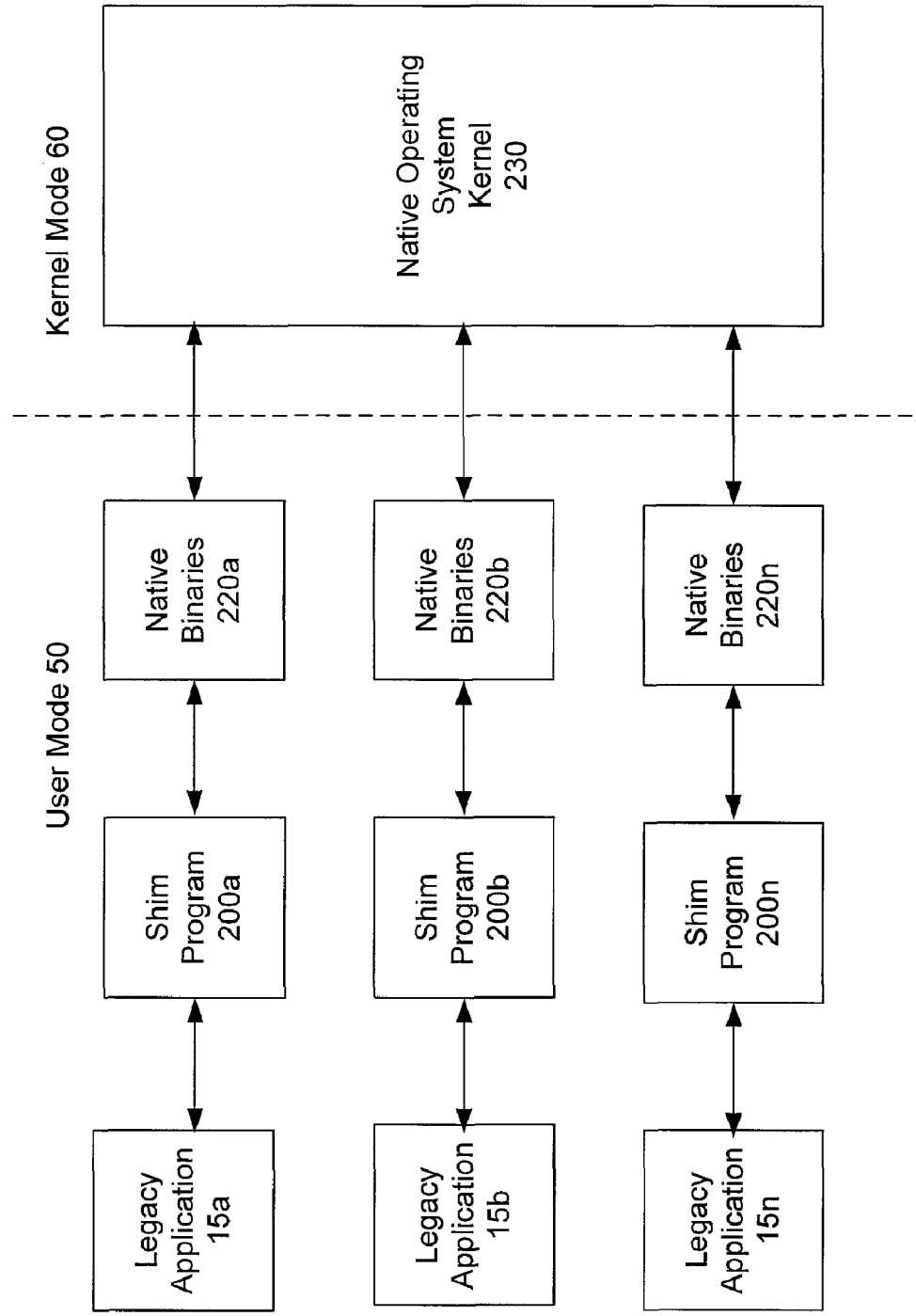
FIG. 2 depicts exemplary execution stacks for legacy applications executing within a native operating system with shim programs.

As described above, a number of compatibility problems may occur when an application executes within an operating system other than the operating system for which the application was initially designed. This may occur, for example, when a legacy application executes within a native operating system. As also described above, one conventional approach to this problem is to load a "shim" program that sits between the legacy application and the native system binaries. Exemplary execution stacks for legacy applications executing within a native operating system with shim programs are illustrated in FIG. 2. Legacy applications 15a-n execute in user mode 50 along with shim programs 200a-n and native binaries 220a-n, while native operating system kernel 230 executes in kernel mode 60. The shim programs 200a-n essentially translate various communications between each respective legacy application 15a-n and the corresponding native binaries 220a-n to provide compatibility between the legacy applications 15a-n and the native operating system kernel 230. As depicted in FIG. 2, because shims are generated on an application specific basis, a separate shim 200a-n must be loaded for each separate legacy application 15a-n.

Figure 3:
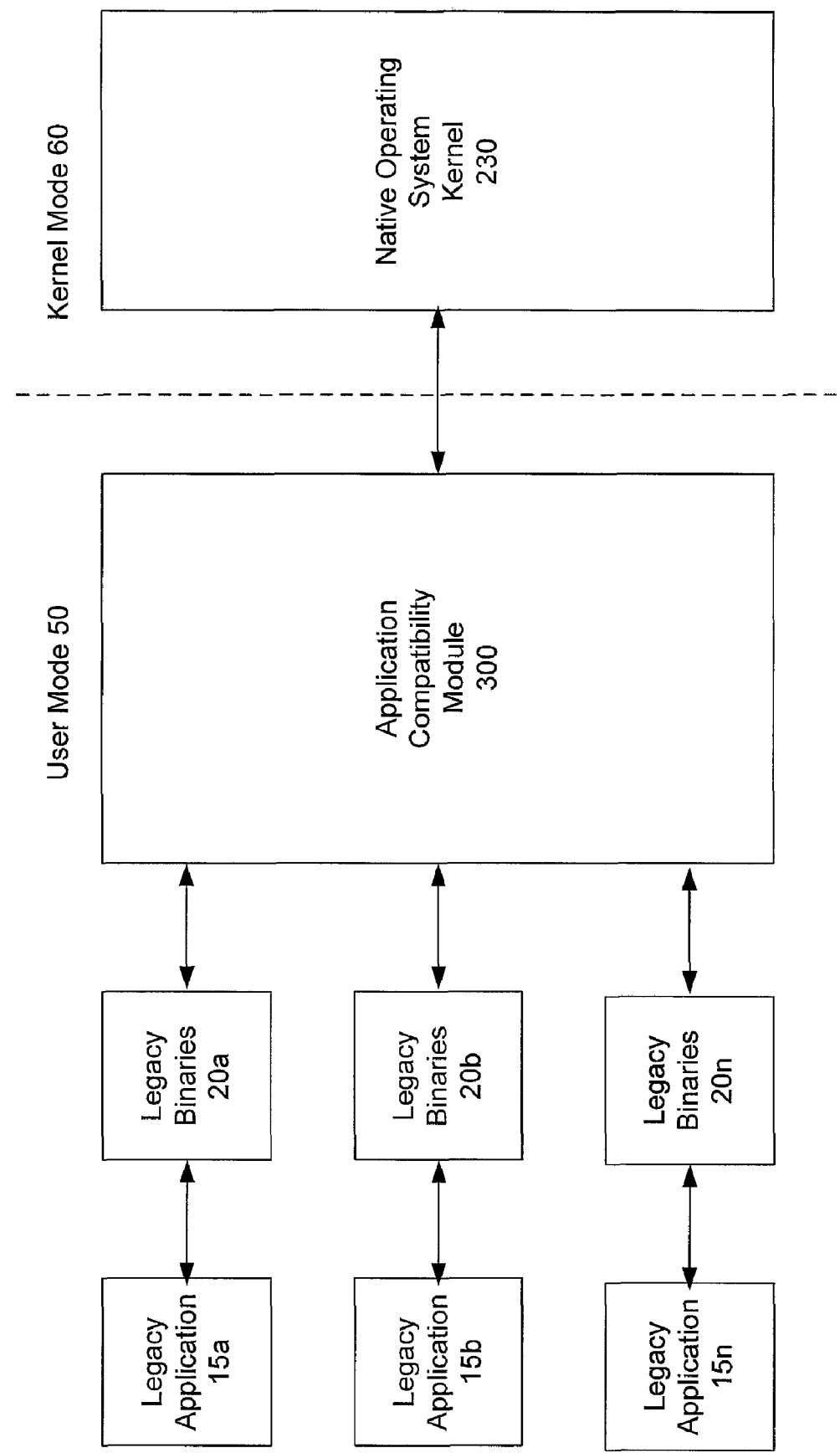
FIG. 3 depicts exemplary execution stacks for legacy applications executing within a native operating system with an application compatibility module.

A scalable approach to the legacy application compatibility problem that enables legacy applications to interact efficiently with a native operating system while at the same time not restricting the accessibility of the native operating system's resources may be accomplished by employing an application compatibility module that provides compatibility between legacy binaries and a native operating system. Exemplary execution stacks for legacy applications executing within a native operating system with an application compatibility module are illustrated in FIG. 3. Legacy applications 15a-n execute in user mode 50 along with legacy binaries 20a-n and application compatibility module 300, while native operating system kernel 230 executes in kernel mode 60. Unlike the stacks of FIG. 2 with separate shims 200a-n loaded for each legacy application 15a-n, the stacks of FIG. 3 employ only a single application compatibility module 300 to execute in connection with multiple different legacy applications 15a-n. Additionally, unlike the stacks of FIG. 2 in which the legacy applications 15a-n use native binaries 220a-n, the application compatibility module 300 of FIG. 3 enables the legacy applications 15a-n to interact with their corresponding legacy binaries 20a-n. Although not shown in FIG. 3, the execution stacks may also include a number of native binaries that process communications between the application compatibility module and the native operating system 230.

The application compatibility module 300 may provide compatibility between legacy binaries 20a-n and native operating system 230 by translating communications between legacy binaries 20a-n and native operating system 230. In particular, the application compatibility module 300 may receive system calls from the legacy binaries 20a-n and translate the system calls into formats that can be understood and processed by the native operating system 230. Additionally, the application compatibility module may receive callbacks and exceptions from the native operating system 230 and translate the callbacks and exceptions into formats that can be understood and processed by the legacy binaries 20a-n.

To assist in the translation of communications between the legacy binaries 20a-n and the native operating system 230, the application compatibility module 300 may access certain types of translation information. The translation information may include, for example, information about system calls, callbacks, exceptions, and any other types of commands or communications that may be employed in connection with an application and/or operating system.

To assist in translating communications from the legacy binaries 20a-n to the native operating system 230, the translation information may include a listing of certain communications that may be generated by the legacy binaries 20a-n and, for each of those communications, a counterpart communication that can be understood and processed by the native operating system 230. In particular, the translation information may include a listing of legacy system calls that can be generated by the legacy applications 15a-n, and, for each legacy system call, a counterpart native system call that can be understood and processed by the native operating system 230.

In one embodiment, the translation information may include a system call translation table. A key column of the system call translation table may list various legacy system calls, and, for each legacy system call listed in the key column, the system call translation table may specify a corresponding native system call. Thus, to translate a legacy system call made by legacy binaries 20a-n, the application compatibility module 300 can access the system call translation table, locate the legacy system call in the key column of the system call translation table, and then identify the corresponding counterpart native system call.

In some circumstances, the native system call may be identical to the legacy system call. In other circumstances, for a particular legacy system call, a counterpart native system call may no longer exist. Flags or other information to identify legacy system calls with non-existent counterpart native system calls may also be included in the system call translation table or any other suitable storage location. When a counterpart native system call no longer exists or has changed in some manner from the corresponding previous legacy system call, the application compatibility module 300 may generate an error message indicating such and submit the error message back to the legacy binaries 20a-n. Additionally or alternatively, the translation information may include thunking code necessary to implement the functionality of the previous legacy system call. The thunking code may be stored in the system call translation table, or alternatively, the system call translation table may include a pointer to another location in which the thunking code is stored. Sometimes, in order to be properly executed, a counterpart native system call may require additional parameters or other data. When a counterpart native system call requires additional parameters or other data, the application compatibility module 300 may gather the necessary information and/or generate a notification requesting this information and submit the notification back to the legacy binaries 20a-n.

In addition to translating communications from the legacy binaries 20a-n to the native operating system 230, the application compatibility module 300 may also translate communications from the native operating system 230 to the legacy binaries 20a-n. To assist in translating communications from the native operating system 230 to the legacy binaries 20a-n, the translation information may also include a listing of certain communications that may be generated by the native operating system 230 and, for each of those communications, a counterpart communication that can be understood and processed by the legacy binaries 20a-n. In particular, the translation information may include a listing of native callbacks that can be generated by the native operating system 230, and, for each native callback, a counterpart set of legacy callback functions that can be understood and processed by the legacy binaries 20a-n.

In one embodiment, the translation information may include a callback dispatch table. A key column of the callback dispatch table may list various native callbacks, and, for each native callback listed in the key column, the callback dispatch table may specify a corresponding set of legacy callback functions. Thus, to translate a native callback made by the native operating system 230, the application compatibility module 300 can access the callback dispatch table, locate the native callback in the key column of the callback dispatch table, and then identify the counterpart legacy callback functions.

In some circumstances, the legacy callback functions may be identical to the native callback functions that would be invoked by the native callback. In other circumstances, one or more of the legacy callback functions may be different than the native callback functions that would be invoked by the native callback. In either case, the corresponding set of legacy callback functions may be stored in the callback dispatch table. In other circumstances, the native callback will implement certain behaviors that do not map to any particular legacy callback functions. In this scenario, the translation information may include thunking code with new functions to implement the new set of behaviors. The thunking code may be stored in the callback dispatch table, or alternatively, the callback dispatch table may include a pointer to another location in which the thunking code is stored. Sometimes, in order to be properly executed by legacy binaries 20a-n, a native callback may require additional parameters or other data from the native operating system 230. When a native callback requires additional parameters or other data, the application compatibility module 300 may gather the necessary information and/or generate a notification requesting this information and submit the notification back to the native operating system 230 and/or the native binaries.

In addition to a callback dispatch table, the translation information accessible to the application compatibility module 300 may also include an exception dispatch table that maps each native exception to the necessary information that is required for the native exception to be understood and processed by legacy binaries 20a-n. In some circumstances, the exception information required by legacy binaries 20a-n may be identical to the exception information that would be required by a native application. In other circumstances, some thunking may be required to convert the native exception into information that can be understood and processed by the legacy binaries 20a-n. This thunking information may be stored in the exception dispatch table, or alternatively, the exception dispatch table may include a pointer to another location in which the thunking information is stored. For example, the layout of a native exception may need to be altered so that it can be understood and processed by legacy binaries 20a-n. In particular, the data regions referenced by the native exception may be different when the exception is delivered to a legacy application 15 as opposed to a native application. In this case, the thunking information would include the appropriate data regions that would apply to the legacy binaries 20a-n.

As should be appreciated, in addition to or as an alternative to tables, any other type of storage mechanism, such as, for example, arrays, may be employed to store translation information for translating system calls, callback, exceptions, or any other type of communication. Additionally, any number of different tables or other storage mechanisms may be employed to store and organize translation information. For example, application compatibility module 300 may be used in connection with multiple legacy applications originally designed for multiple different legacy operating systems. In this scenario, a different set of translation tables or other storage mechanisms may be generated and stored for each different legacy operating system. Unlike shims which are generated on an application by application basis, the translation information employed by the application compatibility module 300 may not be specific to any particular legacy application, but, rather, may include information about system calls, callbacks, exception messages for one or more particular legacy operating systems and any legacy applications that were designed for those legacy operating systems.

The translation information employed by the application compatibility module 300 may be compiled using a number of different possible techniques. For example, in one embodiment, the build processes of one or more legacy operating systems may be altered to allow the emission of information regarding system calls, callback functions, exception information and any other information about these or any other appropriate communications from the legacy operating systems. When the application compatibility module 300 is built on the native build environment, one or more tools may be ran on the native build environment to assemble information for mapping the legacy operating system communications to their counterpart native operating system communications and vice versa. This mapping information may include, for example, but not limited to, the system call translation table, the callback dispatch table, the exception dispatch table and any of the system call, callback and/or exception thunking information set forth above.

An application compatibility module 300 executing on a particular system may retrieve or update translation information at any time by connecting to a translation information database or other suitable information source over a network such as the Internet. Application compatibility module 300 may, for example, be configured to update its translation information at regular intervals, in response to a user command, or upon detecting a new legacy application that was designed for a legacy operating system for which the application compatibility module 300 does not have sufficient translation information.

Figure 4:
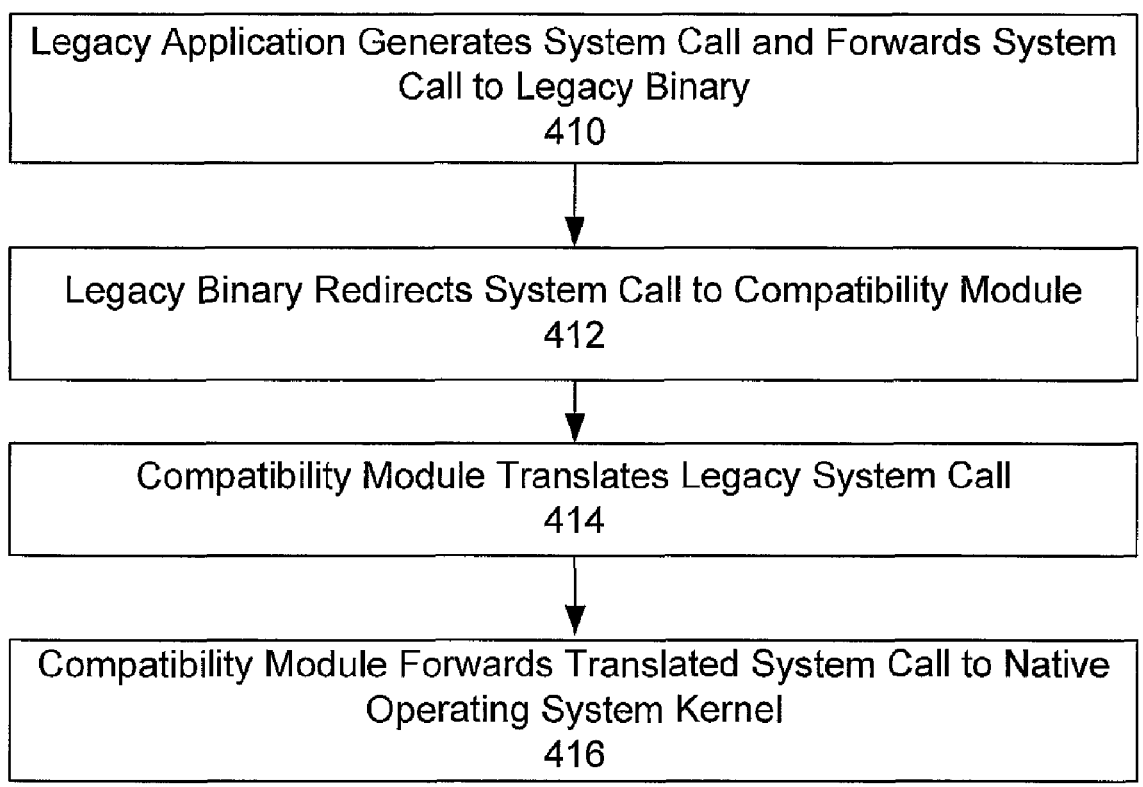
FIG. 4 is a flowchart representing an exemplary method for translating a legacy system call from legacy binaries to a native operating system.

A flowchart representing an exemplary method for translating a legacy system call from the legacy binaries to a native operating system is shown in FIG. 4. At act 410, legacy application 15 generates the legacy system call and forwards the legacy system call to legacy binary 20. At act 412, legacy binary 20 redirects the system call to the application compatibility module 300. In one embodiment, to allow the application compatibility module to hook system call execution coming from the legacy binary 20, each legacy binary 20 may be altered to include a corresponding stub file for use with the application compatibility module 300. The stub file may be used to generate an indirect jump to a memory address instruction rather than the usual system call instruction. The indirect jump address may be initialized by the application compatibility module 300 on thread initialization. For x86 processor architectures, the jump address may be a specific portion of the thread environment block (TEB), which is an internal structure associated with each thread that contains values used to control each thread. A pointer to the TEB may be stored in an FS register or any other suitable location.

At act 414, the compatibility module 300 translates the legacy system call to an appropriate native system call. The application compatibility module 300 may employ translation information such as, for example, but not limited to, a system call translation table such as described above, to assist in the translation process. As set forth above, in some cases, the counterpart native system call may be identical to the previous legacy system call. In other cases, for a particular legacy system call, a counterpart native system call may no longer exist. Flags or other information to identify non-existent counterpart native system calls may be included in the system call translation table or any other suitable storage location. When a counterpart native system call no longer exists or has changed in some manner from the corresponding previous legacy system call, the application compatibility module 300 may employ thunking code necessary to implement the functionality of the previous legacy system call. The thunking code may be stored in the system call translation table, or alternatively, the system call translation table may include a pointer to another location in which the thunking code is stored.

After the legacy system call has been translated to an appropriate native system call, application compatibility module 300 forwards the translated system call to native operating system kernel 230. The translated system call may be forwarded either directly or indirectly to the native operating system kernel 230. In particular, the translated system call may be submitted to one or more native binaries or other appropriate modules prior to being passed to the native operating system kernel 230.

Figure 5:
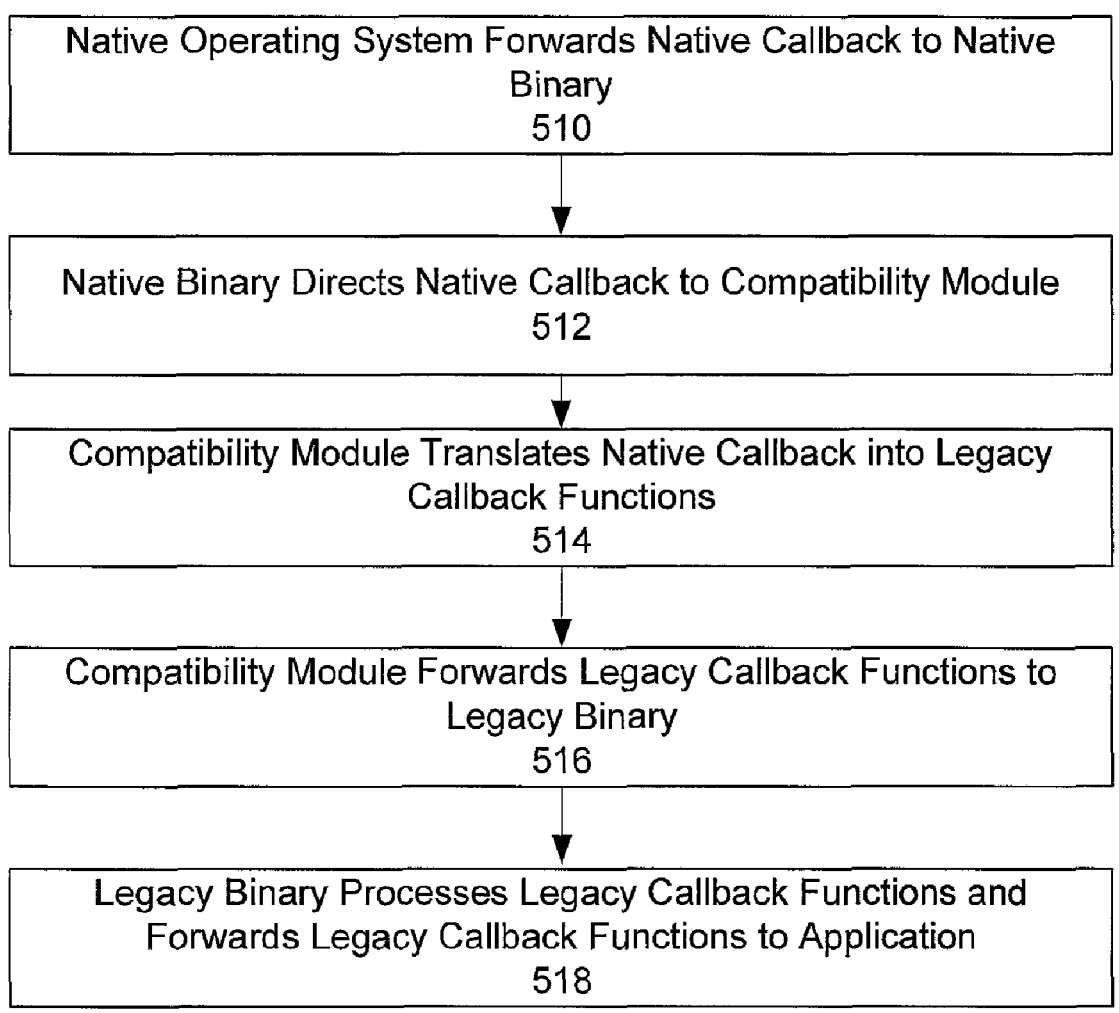
FIG. 5 is a flowchart representing an exemplary method for translating a native callback from a native operating system to legacy binaries.

A flowchart representing an exemplary method for translating a native callback from a native operating system to the legacy binaries is shown in FIG. 5. At act 510, native operating system kernel 230 forwards the native callback to a native binary. At act 512, the native binary directs the callback to application compatibility module 300. At act 514, application compatibility module 300 translates the native callback into a set of legacy callback functions that can be understood and processed by the legacy binaries 20a-n. The application compatibility module 300 may employ translation information such as, for example, but not limited to, a callback dispatch table such as described above, to assist in the translation process. As set forth above, in some cases, the legacy callback functions may be identical to the native callback functions that would be invoked by the native callback. In other cases, one or more of the legacy callback functions may be different than the native callback functions that would be invoked by the native callback. In either case, the corresponding set of legacy callback functions may be stored in the callback dispatch table. In other cases, the native callback may implement certain behaviors that do not map to any particular legacy callback functions. In this scenario, the translation information may include thunking code with new functions to implement the new set of behaviors. The thunking code may be stored in the callback dispatch table, or alternatively, the callback dispatch table may include a pointer to another location in which the thunking code is stored.

At act 516, application compatibility module 300 forwards the legacy callback functions, along with any other appropriate data, to the legacy binaries 20a-n. At act 518, the legacy binaries 20a-n process the legacy callback functions and/or other appropriate data in some manner, and then forward the legacy callback functions and other appropriate data to the legacy application 15.

Figure 6:
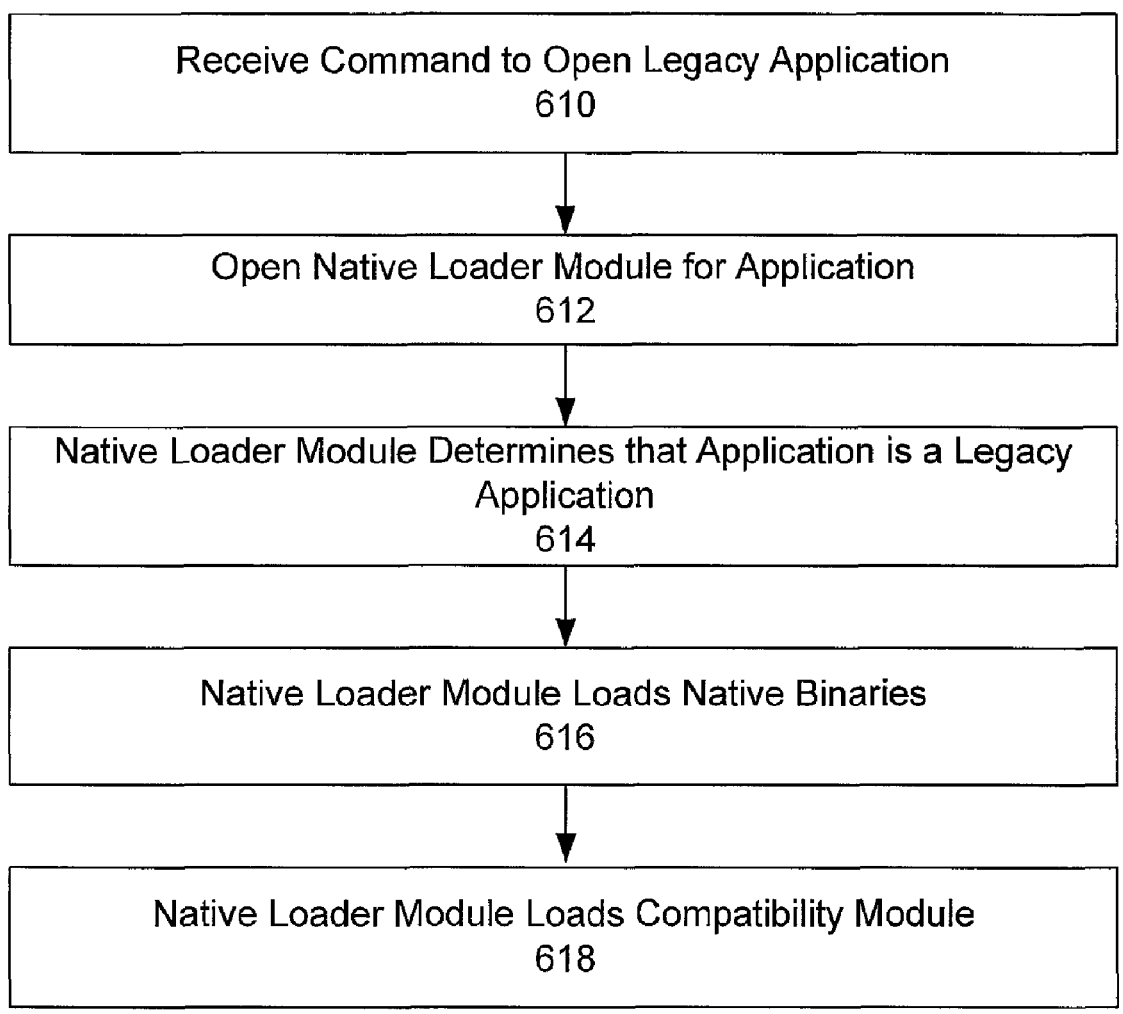
FIG. 6 is a flowchart representing an exemplary method for loading an application compatibility module and legacy binaries.

As should be appreciated, exceptions may be sent from the native operating system kernel 230 to the legacy binaries 20a-n following a similar, although not necessarily identical, process to that which is depicted in FIG. 6. As set forth above, exceptions may be translated and dispatched by application compatibility module 300 using an exception dispatch table or other suitable information for translating a native exception into information that can be understood and processed by legacy binaries 20a-n.

FIG. 6 is a flowchart representing an exemplary method for loading an application compatibility module 300 and legacy binaries 20a-n. At act 610, a command is received to open a legacy application 15. In response to this command, a native binary loader module is opened for the application. At act 612, the native loader module determines that the application is a legacy application rather than an application designed for the native operating system. Responsive to this determination, at act 614, the native loader module loads one or more legacy binaries 20a-n that are necessary and appropriate for execution along with the legacy application. At act 616, the native loader module loads the application compatibility module 300.

It should be noted here that, although the above description refers to "legacy applications" and a "native operating system," the techniques described herein are not limited to legacy applications executing within a native operating system. Rather, the techniques described herein are intended to apply to any situation in which an application is executing within an operating system that is different from the operating system for which the application was initially designed. This may include, for example, but not limited to, situations in which an application is executing within an operating system which is either a newer or an older version of the operating system for which the application was initially designed.

Figure 7:
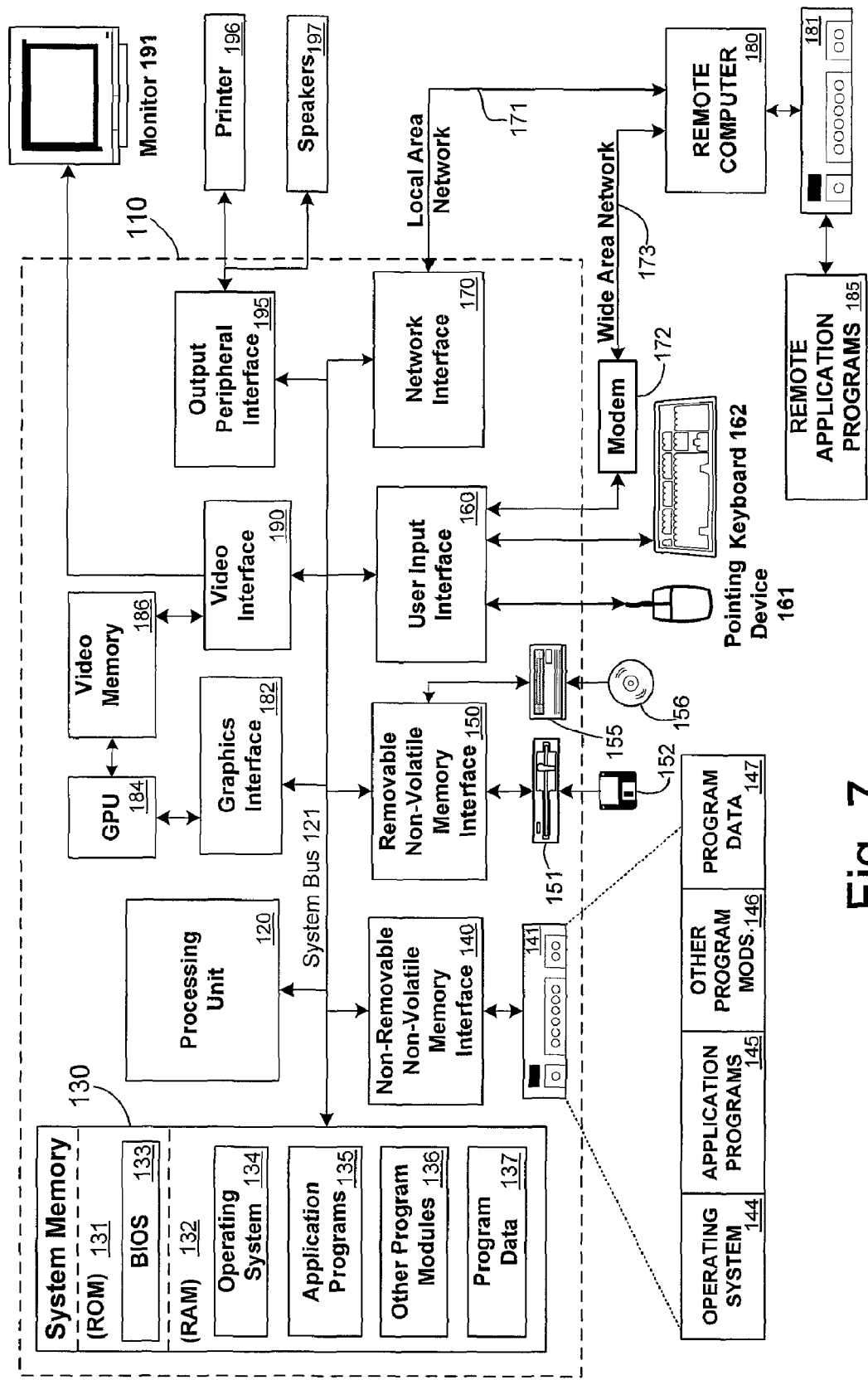
FIG. 7 is a block diagram representing an exemplary computing device.

FIG. 7 illustrates an example of a suitable computing system environment 100 in which the subject matter described above may be implemented. The computing system environment 100 is only one example of a suitable computing environment and is not intended to suggest any limitation as to the scope of use or functionality of the subject matter described above. Neither should the computing environment 100 be interpreted as having any dependency or requirement relating to any one or combination of components illustrated in the exemplary operating environment 100.

With reference to FIG. 7, computing system environment 100 includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media include both volatile and nonvolatile, removable and non-removable media implemented in any method or technology for storage of information such as computer readable instructions, data structures, program modules or other data. Computer storage media include, but are not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other medium which can be used to store the desired information and which can be accessed by computer 110. Communication media typically embody computer readable instructions, data structures, program modules or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared and other wireless media. Combinations of any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 7 illustrates operating system 134, application programs 135, other program modules 136, and program data 137.

The computer 110 may also include other removable/non-removable, volatile/nonvolatile computer storage media. By way of example only, FIG. 7 illustrates a hard disk drive 141 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156, such as a CD-RW, DVD-RW or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 7 provide storage of computer readable instructions, data structures, program modules and other data for the computer 110. In FIG. 7, for example, hard disk drive 141 is illustrated as storing operating system 144, application programs 145, other program modules 146 and program data 147. Note that these components can either be the same as or different from operating system 134, application programs 135, other program modules 136 and program data 137. Operating system 144, application programs 145, other program modules 146 and program data 147 are given different numbers here to illustrate that, at a minimum, they are different copies. A user may enter commands and information into the computer 110 through input devices such as a keyboard 162 and pointing device 161, such as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus 121, but may be connected by other interface and bus structures, such as a parallel port, game port or a universal serial bus (USB). A graphics interface 182 may also be connected to the system bus 121. One or more graphics processing units (GPUs) 184 may communicate with graphics interface 182. A monitor 191 or other type of display device is also connected to the system bus 121 via an interface, such as a video interface 190, which may in turn communicate with video memory 186. In addition to monitor 191, computers may also include other peripheral output devices such as speakers 197 and printer 196, which may be connected through an output peripheral interface 195.

The computer 110 may operate in a networked or distributed environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 7. The logical connections depicted in FIG. 7 include a local area network (LAN) 171 and a wide area network (WAN) 173, but may also include other networks/buses. Such networking environments are commonplace in homes, offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 7 illustrates remote application programs 185 as residing on memory device 181. It will be appreciated that the network connections shown are exemplary and other means of establishing a communications link between the computers may be used.

Although the subject matter has been described in language specific to the structural features and/or methodological acts, it is to be understood that the subject matter defined in the appended claims is not necessarily limited to the specific features or acts described above. Rather, the specific features or acts described above are disclosed as example forms of implementing the claims.

What is claimed:
1. A computer system comprising:
a processor;
a first operating system executing on the computer system;
an application executing within the first operating system, the application designed for execution within a second operating system;

at least one binary module executing within the first operating system, the at least one binary module being in communication with the application, the at least one binary module designed for execution within the second operating system;

an application compatibility module executing within the first operating system, the application compatibility module for translating communications between the at least one binary module and the first operating system; and a loader module that determines that the application is designed for execution within the second operating system different from the first operating system and that responsively loads the application compatibility module.

2. The computer system of claim 1, wherein the first operating system is a newer version of the second operating system.

3. The computer system of claim 1, wherein the application compatibility module translates system calls made by the at least one binary module into system calls compatible with the first operating system.

4. The computer system of claim 3, further comprising a table accessible to the application compatibility module, the table listing at least one second system call compatible with the second operating system and, for each listed second system call, a corresponding first system call compatible with the first operating system.

5. The computer system of claim 1, wherein the application compatibility module translates callbacks made by the first operating system into a set of at least one callback functions compatible with the at least one binary module.

6. The computer system of claim 5, further comprising a table accessible to the application compatibility module, the table listing at least one callback that is generated by the first operating system and, for each listed callback, a corresponding set of at least one callback functions compatible with the at least one binary module.

7. The computer system of claim 1, wherein the application compatibility module translates exceptions generated by the first operating system into exceptions compatible with the at least one binary module.

8. The computer system of claim 7, further comprising a table accessible to the application compatibility module, the table listing at least one first exception that is generated by the first operating system and, for each listed first exception, a corresponding second exception compatible with the at least one binary module.

9. The computer system of claim 1, wherein a single application compatibility module translates communications between a plurality of different applications and the first operating system.

10. The computer system of claim 9, wherein a single application compatibility module translates communications between a plurality of applications designed for a plurality of different operating systems and the first operating system.

11. A computer readable storage medium having stored thereon computer executable instructions for performing steps comprising:
receiving a command to open an application within a first operating system;
responsively executing a loader module for the application;
determining by the loader module that the application is designed for execution within a second operating system different from the first operating system;
responsively loading by the loader module an application compatibility module;
receiving by a binary module a communication from the application, the binary module also designed for execution within the second operating system;
redirecting by the binary module the communication to the application compatibility module; and
translating by the application compatibility module the communication into a communication that is compatible with the first operating system.

12. The computer readable storage medium of claim 11, wherein the first operating system is a newer version of the second operating system.

13. The computer readable storage medium of claim 11, wherein the communication is a system call.

14. The computer readable storage medium of claim 13, wherein translating comprises accessing a table listing at least one first system call compatible with the first operating system and, for each listed first system call, a corresponding second system call compatible with the second operating system.

15. A computer readable storage medium having stored thereon computer executable instructions for performing steps comprising:
receiving a command to open an application within a first operating system;
responsively executing a loader module for the application;
determining by the loader module that the application is designed for execution within a second operating system different from the first operating system;
responsively loading by the loader module an application compatibility module;
receiving by the application compatibility module a communication from the first operating system;
translating by the application compatibility module the communication into a communication that is understandable to a binary module designed for execution within the second operating system; and
submitting the translated communication to the binary module, the binary module being in communication with the application.

16. The computer readable storage medium of claim 15, wherein the first operating system is a newer version of the second operating system.

17. The computer readable storage medium of claim 15, wherein the communication is a callback.

18. The computer readable storage medium of claim 15, wherein the communication is an exception.

* * * * *